United States Patent [19]

Oyama et al.

[11] Patent Number: 5,288,376

[45] Date of Patent: Feb. 22, 1994

[54] PREPARATION OF PERFLUOROOLIGOETHER IODIDES

[75] Inventors: Masayuki Oyama; Noriyuki Koike, both of Gunma; Toshio Takago, Annaka, all of Japan

[73] Assignee: Shin-Etsu Chemical Co., Ltd., Tokyo, Japan

[21] Appl. No.: 17,952

[22] Filed: Feb. 16, 1993

Related U.S. Application Data

[63] Continuation of Ser. No. 748,615, Aug. 22, 1991, abandoned.

[30] Foreign Application Priority Data

Aug. 23, 1990 [JP] Japan .................................. 2-222090

[51] Int. Cl.$^5$ ............................................. G07B 39/00
[52] U.S. Cl. ........................ 204/157.63; 204/157.92; 522/163; 522/181; 522/913; 522/914
[58] Field of Search ..................... 204/157.92, 157.63; 522/163, 178, 914, 913, 181; 568/684, 695

[56] References Cited

U.S. PATENT DOCUMENTS 4,859,299  8/1989  Kobayashi et al. ............ 204/157.92

FOREIGN PATENT DOCUMENTS 0348948  1/1990  European Pat. Off. .

OTHER PUBLICATIONS

Harris J. F., J. Org. Chem., (30), pp. 2182-2190 (1965) The Photolysis of Polyfluoroacyl Fluorides, Chlorides, & Bromides.
Database WPIL, Week 8811, Derwent Publications Ltd., London, GB; 2-88.
The Journal of Organic Chemistry, vol. 30, No. 7 (Jul. 1965), pp. 2182-2190, J. F. Harris, "The Photolysis of Polyfluoroacyl Fluorides, Chlorides, and Bromides".

*Primary Examiner*—Kathryn Gorgos
*Attorney, Agent, or Firm*—Millen, White, Zelano, & Branigan

[57] ABSTRACT

A perfluorooligoether iodide is prepared by exposing a perfluoropolyether carboxylic iodide to UV light.

9 Claims, 2 Drawing Sheets

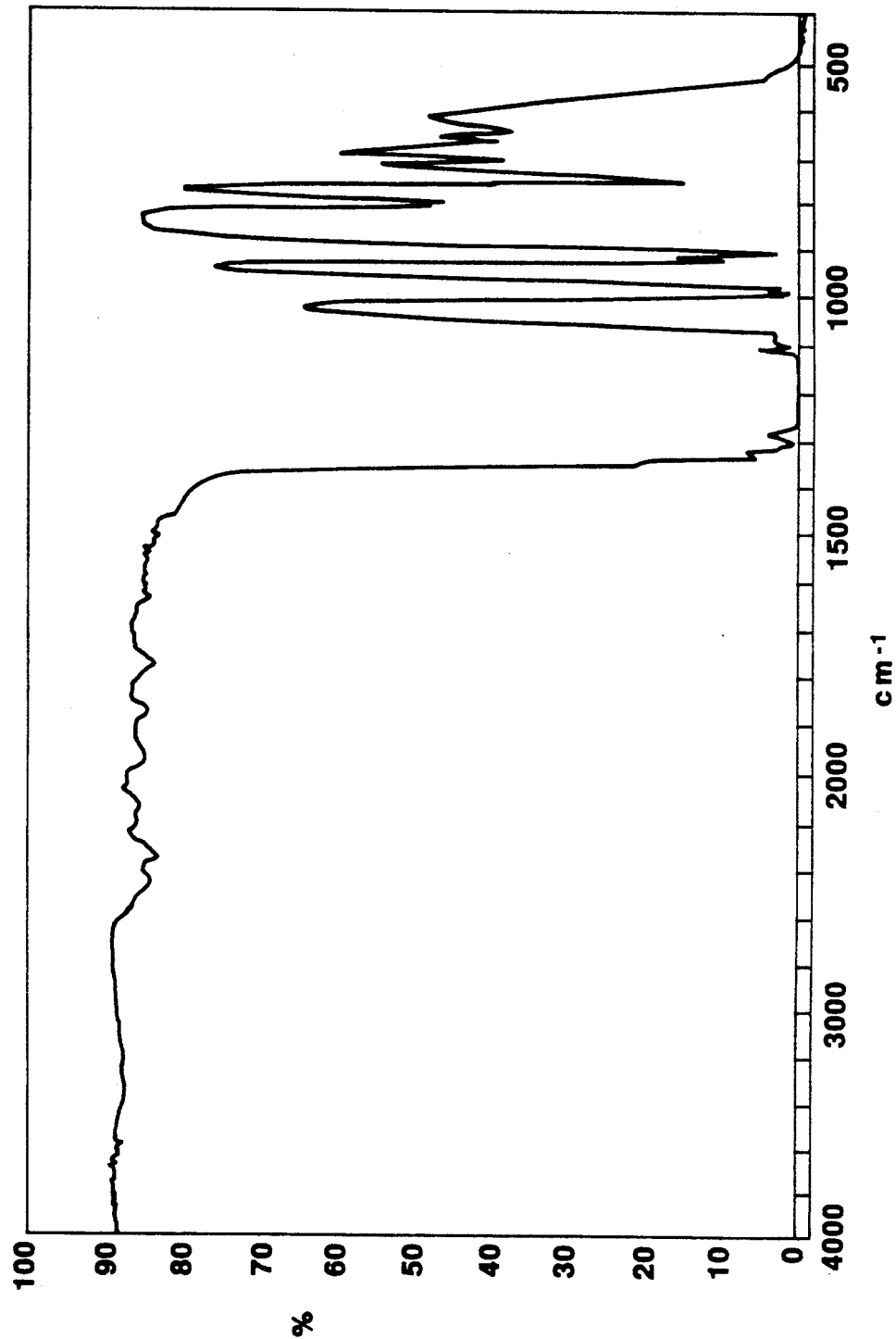

PREPARATION OF PERFLUOROOLIGOETHER IODIDES

This application is a continuation of application Ser. No. 07/748,615, filed Aug. 22, 1991, now abandoned.

This invention relates to a commercially advantageous method for preparing perfluorooligoether iodides which are useful intermediates for the synthesis of fluoro resins, fluoro rubbers, and fluoro surfactants.

BACKGROUND OF THE INVENTION

In the past, methods for preparing perfluoroalkyl iodides by telomerization of tetrafluoroethylene with trifluoromethyl iodide or by deriving from alcohols were commercially used in practice.

However, no commercially acceptable methods have been developed for the preparation of perfluorooligoether iodides of the following general formula (II):

 (II)

wherein Rf is a perfluoroalkyl group having 1 to 10 carbon atoms and letter n is an integer of from 0 to 100, which are useful intermediates for the synthesis of fluoro resins, fluoro rubbers, and fluoro surfactants.

In the prior art, perfluorooligoether iodides are prepared as shown by the following reaction scheme by starting with a perfluorooligoether carboxylic fluoride of the following formula (III), subjecting the reactant to hydrolysis to form a perfluorooligoether carboxylic acid, reacting it with silver oxide to form a perfluorooligoether carboxylic silver salt, and subjecting the salt to pyrolysis in the presence of iodine to thereby form a perfluorooligoether iodide of formula (II) (see Japanese Patent Application Kokai No. 441/1988).

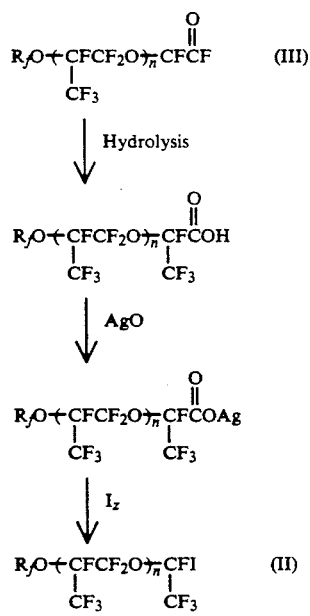

However, several problems must be solved before this process can be commercially practiced. The end product, perfluorooligoether iodide is recovered only in yields of about 70 to 85%. The intermediate or silver salt is often a solid which is difficult to handle. The use of expensive silver necessitates silver recovery from a commercial standpoint. The overall process involves three steps, during which toxic hydrogen fluoride evolves. Pyrolysis reaction must be carried out before the end product can be obtained. Also, economical problems arise from the use of expensive reactants and increased installation cost.

There is a need for the commercially advantageous manufacture of perfluoropolyether while overcoming the above-mentioned problems.

SUMMARY OF THE INVENTION

We have found that by effecting halogen exchange reaction between a perfluoropolyether carboxylic fluoride of formula (III):

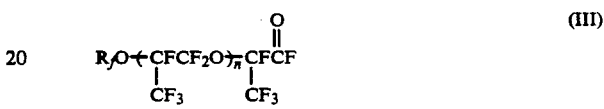
 (III)

wherein Rf and n as defined above and a metal iodide of the general formula (IV):

$$MI_a \quad (IV)$$

wherein m is a metal atom and letter a is the valence of the metal atom, there is obtained a novel perfluoropolyether carboxylic iodide of the general formula (I):

 (I)

wherein Rf and n are as defined above. By exposing the perfluoropolyether carboxylic iodide of formula (I) to ultraviolet light, carbon monoxide removal readily takes place to produce an end product, perfluoropolyether iodide of formula (II):

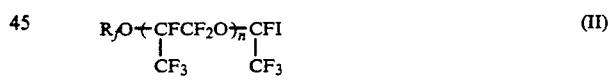
 (II)

wherein Rf and n are as defined above in high yields.

More particularly, since the reaction between the compounds of formulae (III) and (IV) proceeds in a simple manner even at atmospheric pressure and room temperature without forming a by-product, a novel perfluoropolyether carboxylic iodide of formula (I) is obtained in high yields. This novel perfluoropolyether carboxylic iodide releases carbon monoxide upon exposure to ultraviolet light at atmospheric pressure and room temperature and converts into an end product, perfluoropolyether iodide of formula (II) at a conversion rate of 95% or higher without forming a by-product. The step of ultraviolet exposure requires merely to irradiate ultraviolet light while no other special operation is needed. The reaction system can be increased to any desired scale in theory insofar as a tank for receiving the reaction solution is installed in the system.

As compared with the prior art process, the perfluoropolyether perfluorooligoether iodide preparing method of the present invention has many advantages.

(1) Very high yield.
(2) No use of expensive silver oxide.
(3) A simplified process.
(4) No evolution of toxic hydrogen fluoride during the process.
(5) Low reaction temperature.
(6) The intermediate or perfluoropolyether carboxylic iodide of formula (I) is liquid at room temperature and can be isolated by distillation if it has a low molecular weight.

Therefore, the present method allows the perfluoropolyether iodide to be prepared with many commercial benefits.

BRIEF DESCRIPTION OF THE DRAWINGS

FIG. 2 is a chart showing the IR spectrum of a perfluoropolyether iodide obtained in Example.

DETAILED DESCRIPTION OF THE INVENTION

Figure 1:
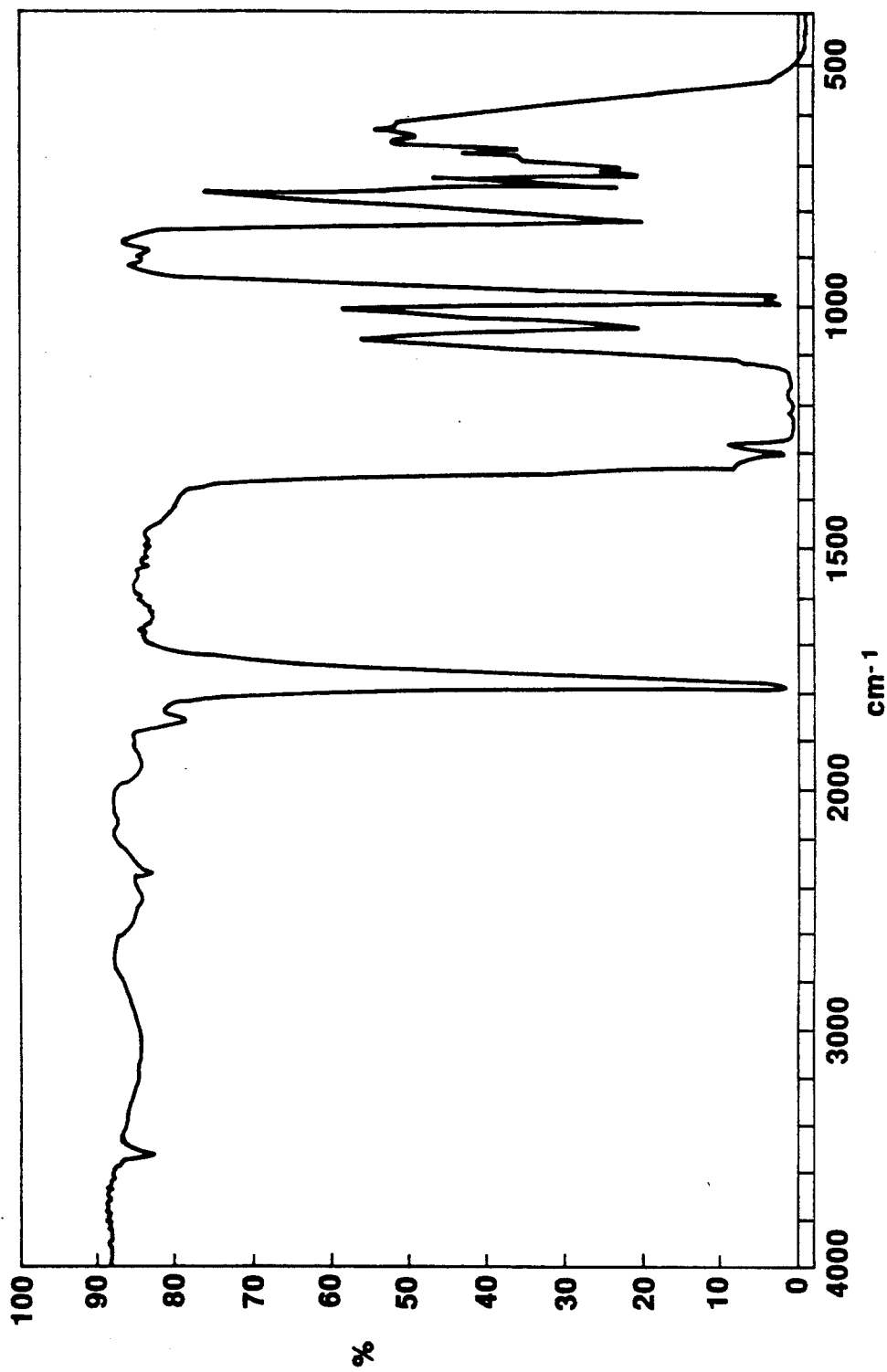
FIG. 1 is a chart showing the IR spectrum of a perfluoropolyether carboxylic iodide obtained in Example.

The present invention is intended to prepare a perfluoropolyether iodide of formula (II) by exposing a perfluoropolyether carboxylic iodide of formula (I) to ultraviolet light. The starting reactant, that is, perfluoropolyether carboxylic iodide of formula (I) is obtained by effecting halogen exchange reaction between a perfluoropolyether carboxylic fluoride and a metal iodide.

The perfluoropolyether carboxylic fluorides are compounds of the general formula (III):

$$R_fO(CFCF_2O)_n\underset{CF_3}{CFCF}=O \quad (III)$$

In formula (III), Rf is a perfluoroalkyl group having 1 to 10 carbon atoms, for example, trifluoromethyl, pentafluoroethyl, heptafluoropropyl, and heptafluoroisopropyl groups. Letter n is an integer of from 0 to 100, preferably from 0 to 30. The perfluoropolyether carboxylic fluorides of formula (III) may be prepared by any conventional well-known methods as disclosed in U.S. Pat. Nos. 3,250,808 and 3,322,826.

With the perfluoropolyether carboxylic fluorides of formula (III) are reacted metal iodides of the general formula (IV):

$$MI_a \quad (IV)$$

wherein M is a metal atom and letter a is the valence of the metal atom. The metal iodides include alkali metal iodides such as LiI and NaI, alkaline earth metal iodides such as $MgI_2$ and $CaI_2$, and other metal iodides such as $AlI_3$. The metal iodide is preferably used in such amounts that the molar amount of iodine in the metal iodide is 1 to 1.2 times the moles of the perfluoropolyether carboxylic fluoride of formula (III). For example, the alkali metal iodide is 1 to 1.2 mol and the alkaline earth metal iodide is 0.5 to 0.6 mol per mol of the formula (III) compound.

These reactants are reacted, for example, by adding a polar solvent to the perfluoropolyether carboxylic fluoride of formula (III) and with stirring, adding thereto the metal iodide in increments. The preferred polar solvents used herein are aprotic solvents such as diethyl ether, diisopropyl ether, dibutyl ether, and acetonitrile.

The solvents are preferably used in amounts of about 2 to 10% by weight of the alkali metal iodide or about 4 to 20% by weight of the alkaline earth metal iodide. The reaction temperature generally ranges from 0° C. to 100° C., preferably 20° C. to 50° C. and the reaction time generally ranges from about 2 to about 50 hours, preferably from about 5 to about 10 hours. Since both the reactants and the product are prone to hydrolysis, it is recommended to thoroughly purge the reactor with an inert gas such as nitrogen and argon. At the end of reaction, the metal fluoride is removed by filtration and then, the perfluoropolyether carboxylic iodide of formula (I):

$$R_fO(CFCF_2O)_n\underset{CF_3}{CFCl}=O \quad (I)$$

wherein Rf and n are as defined above can be recovered from the reaction solution in high yields by distillation isolation or by distilling off the solvent.

The resultant perfluoropolyether carboxylic iodide of formula (I) can be readily converted into an end product, perfluoropolyether iodide of formula (II) in high yields simply by exposing the former to UV light, causing it to release carbon monoxide.

For UV exposure, a UV irradiation apparatus having a high pressure mercury lamp with a cooling quartz jacket may be used. Reaction is conducted by exposing the charge in the photo-reactor to UV at a wavelength of 180 to 380 nm, preferably 200 to 300 nm at a temperature of 0° to 60° C., preferably room temperature for about 2 to about 30 hours. There is no need for solvent although the charge may be diluted with a stable organic solvent if desired. Such solvents are perfluorooctane, perfluoroisononane and the like. Also preferably, this reaction is effected in an inert gas atmosphere such as nitrogen and argon.

With respect to the photo-reaction of perfluoroalkyl carboxylic halides, reference is made to *Hassow*, J. Org. Chm., 30, 2182 (1965), reporting the synthesis of RfBr in high yields by UV exposure of perfluorocarboxylic bromide RfCOBr.

The perfluoropolyether iodides of formula (II):

$$R_fO(CFCF_2O)_n\underset{CF_3}{CFI} \quad (II)$$

which are obtained in this way are useful intermediates for the synthesis of fluoro resins, fluoro rubbers and fluoro surfactants.

There has been described a commercially advantageous method for preparing perfluorooligoether iodides of formula (II) in high yields which are useful intermediates for the synthesis of fluoro resins, fluoro rubbers and fluoro surfactants.

EXAMPLE

Examples of the present invention are given below by way of illustration and not by way of limitation.

Example

A ½- liter four-necked flask equipped with a mechanical stirrer, reflux condenser, and gas inlet tube was charged with 400 grams (0.80 mol) of a perfluoropolyether carboxylic fluoride of the formula:

and 8 grams acetonitrile. With stirring the contents, 118 grams (0.88 mol) of lithium iodide was added to the flask in several portions in an argon stream. The lithium iodide was added in such a controlled rate that the temperature of the contents did not exceed 40° C. At the end of addition, the contents were stirred for a further 15 hours.

The contents were passed through a glass filter to remove the solids. Distillation of the filtrate yielded 421 grams of a fraction having a boiling point of 87°–90° C./80 mmhg. The yield was 87%.

The product was analyzed by elemental analysis,, GC-MS, IR spectroscopy,, and $^{19}$F-NMR. The results are shown below.

|  | Elemental analysis | | | |
| --- | --- | --- | --- | --- |
|  | C | F | I | O |
| Calcd., % | 17.82 | 53.30 | 20.96 | 7.92 |
| Found, % | 17.79 | 53.37 | 20.91 | 7.93 |

GC - MS: m/e (M+) molecular weight 606

IR spectroscopy:

FIG. 1 is a chart showing the IR spectrum of the product. It is observed that the absorption peak at 1890 cm$^{-1}$ attributable to —CO—F disappeared and a peak newly developed at 1785 cm$^{-1}$ attributable to —CO—I.

$^{19}$F - NMR: δ(ppm): 66.5 (m. 1F., CF); 52.8 (m, 2F, CF$_2$); 41.0 (m, 1F, CF-COI); - 1.5–7.1 (m, 13F, —CF$_3$, CF$_2$O—).

With these measurement results, the product was identified to be a perfluoropolyether carboxylic iodide of the following formula.

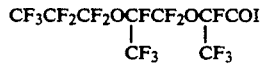

Next, a UV irradiation apparatus was equipped with a high pressure mercury lamp with a cooling quartz jacket. The apparatus was charged with 200 grams (0.33 mol) of the perfluoropolyether carboxylic iodide, which was exposed to UV light while stirring with a magnetic stirrer. The lamp was operated at a power of 100 W and a wavelength of 220 to 380 nm. Reaction was continued for 16 hours at 35 to 40° C. in an argon stream. At the end of reaction, the reaction product was distilled, obtaining 181 grams of a fraction having a boiling point of 78.5° C./101 MmHg. The yield was 95%.

The product was analyzed by elemental analysis,, GC- MS,, IR spectroscopy,, and $^{19}$F-NMR. The results are shown below.

|  | Elemental analysis | | | |
| --- | --- | --- | --- | --- |
|  | C | F | I | O |
| Calcd., % | 16.61 | 55.88 | 21.79 | 5.54 |
| Found, % | 16.57 | 55.91 | 21.92 | 5.60 |

GC-MS: m/e (M+) molecular weight 578

IR spectroscopy:

FIG. 2 is a chart showing the IR spectrum of the product. It is observed that the absorption peak at 1785 cm$^{-1}$ attributable to —CO—I disappeared.

$^{19}$F-NMR: δ(ppm): 69.9 (m, 1F, CF); 59.8 (m, 2F, CF$_2$); 3.7-15.8 (m, 13F, —CF$_3$, —CF$_2$O—) —0.3 (m, 1F, CFI).

With these measurement results, the product was identified to be a compound of the following formula.

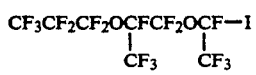

We claim:

1. A method for preparing a perfluoropolyether iodide of the formula

by reacting a perfluoropolyether carboxylic fluoride of the formula

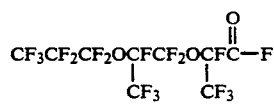

with a metal iodide of the formula MIa, wherein M is a metal atom and a is the valence of the metal, to form a perfluoropolyether carboxylic iodide of the formula (I)

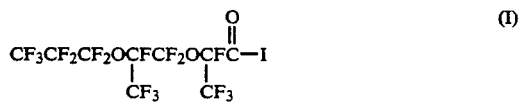

and exposing the perfluoropolyether carboxylic iodide of formula (I) to ultraviolet light at a wavelength of 220–280 nm at a temperature of 0°–60° C. for about 2 to about 30 hours.

2. A method of claim 1, wherein the perfluoropolyether carboxylic iodide of Formula (I) is exposed to ultraviolet light at a wavelength of 180–380 nm.

3. A method for preparing a perfluoropolyether iodide of the general formula (II):

wherein

Rf is a perfluoroalkyl group having 1 to 10 carbon atoms, and n is an integer of from 0 to 100, said method comprising the steps of reacting a perfluoropolyether carboxylic fluoride of formula (III):

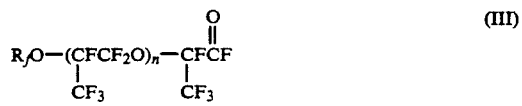

with a metal iodide of the formula (IV)

MIa       (IV)

to form a perfluoropolyether carboxylic iodide of formula (I):

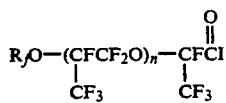

where M is a metal atom, a is the valence of the metal tom, and Rf and n are as defined above, and exposing the perfluoropolyether carboxylic iodide of formula (I) to ultraviolet light at a temperature of 0°–60° C. for about 2–30 hours to produce the perfluoropolyether of formula (II).

4. A method of claim 3, wherein $R_f$ is trifluoromethyl, pentafluoromethyl, heptafluoropropyl, or heptafluoroisopropyl, and n is an integer of from 0 to 30.

5. A method of claim 3, wherein the metal iodides are selected from alkali metal iodides, alkaline earth metal iodides, and aluminum iodides.

6. A method of claim 3, wherein the amount of iodine in the metal iodide is 1 to 1.2 mols per mol of perfluoropolyether carboxylic fluoride of Formula (III).

7. A method of claim 3, wherein the reaction between the perfluoropolyether carboxylic fluoride and metal iodide takes place in a polar aprotic solvent selected from diethyl ether, diisopropyl ether, dibutyl ether, and acetonitrile.

8. A method of claim 3, wherein the reaction between the perfluoropolyether carboxylic fluoride of Formula (III) and metal iodide takes place a temperature within the range of 0°–100° C. from 2–50 hours.

9. A method of claim 3, wherein the perfluoropolyether carboxylic iodide of Formula (I) exposed to ultraviolet light at a wavelength of 180–380 nm.